United States Patent [19]
Smith, Jr.

[11] 4,089,751
[45] May 16, 1978

[54] PROCESS FOR RECOVERING HIGH PURITY CIS-1,4-DICHLOROBUTENE-2

[75] Inventor: Lawrence A. Smith, Jr., Houston, Tex.

[73] Assignee: Denka Chemical Corporation, Houston, Tex.

[21] Appl. No.: 652,832

[22] Filed: Jan. 27, 1976

[51] Int. Cl.$^2$ .......................... B01D 3/10; C07C 21/00
[52] U.S. Cl. ................................ 203/74; 203/67; 203/81; 260/654 S
[58] Field of Search ................ 203/67, 71, 81, 84, 203/74; 260/654 S, 655, 652 P, 654 H

[56] References Cited
U.S. PATENT DOCUMENTS

| | | | |
|---|---|---|---|
| 2,850,549 | 9/1958 | Ray | 260/652 P |
| 2,861,084 | 11/1958 | Starcher | 260/654 H |
| 2,912,471 | 11/1959 | Capp et al. | 260/654 H |
| 2,928,884 | 3/1960 | Bellringer et al. | 260/654 H |
| 2,948,760 | 8/1960 | Capp et al. | 260/654 H |
| 3,899,399 | 8/1975 | Long et al. | 260/652 P |
| 3,901,950 | 8/1975 | Richards et al. | 260/655 |
| 3,914,167 | 10/1975 | Ivy et al. | 260/654 H |

*Primary Examiner*—Wilbur L. Bascomb, Jr.
*Attorney, Agent, or Firm*—Kenneth H. Johnson

[57] ABSTRACT

The relative volatility of cis-1,4-dichlorobutene-2 to trans-1,4-dichlorobutene-2 is increased when these two isomers are fractionated in the presence of 3,4-dichlorobutene-1.

3 Claims, 3 Drawing Figures

PROCESS FOR RECOVERING HIGH PURITY CIS-1,4-DICHLOROBUTENE-2

BACKGROUND OF THE INVENTION

The present invention relates to a method of recovering cis-1,4-dichlorobutene-2 (1,4-DCB-2) in high purity. More particularly, the present invention relates to a distillation process.

Cis-1,4-dichlorobutene-2 is one of the products resulting from the addition of chlorine to butadiene, for example, the process of chlorinating butadiene to give a mixture of 3,4-dichlorobutene-1 and cis, trans-1,4-dichlorobutene-2, isomerizing the latter to 3,4-dichlorobutene-1 and dehydrochlorinating the 3,4-dichlorobutene-1 to chloroprene is well known. All three isomers are in equilibrium with one another so that it is theoretically possible to convert the entire dichlorobutene mixture into any one isomer, however in a commercial size operation there still may be a substantial quantity of by-product.

Previously cis-1,4-dichlorobutene-2 was a by-product which was desirably converted to the chloroprene precursor, however, recently the cis-1,4-DCB-2 has been found to be useful as a precursor for cis-1,4-dichloro-2,3-epoxybutane, which has lead to a new class of polyethers (U.S. Pat. No. 3,065,188).

The cis and trans-1,4-dichloro-2,3-epoxybutanes useful in the polymerizations may be prepared by the peracetic acid epoxidation of the respective dichloro-2-butenes. Such a process is described in U.S. Pat. No. 3,150,154. Cis-reaction produces the cis-oxide and trans-reactant produces the trans-oxide.

Recent studies as reported by E. J. Vandenberg in a paper entitled "A New Class of Polyethers - Poly (1,4-Dichloro-2,3-Epoxybutane)S - Synthesis, Mechanism and Property Aspects" presented at the IUPAC Microsymposium on "Polymerization of Heterocycles", Jablonna, Poland, June 23–25, 1975 established that the cis form of the oxide produced the most valuable polymers.

The separation of the cis-1,4-dichlorobutene-2 may be carried out from a racemic mixture of cis- and trans-1,4-dichlorobutene-2 and 3,4-dichlorobutene-1. The separation of the 3,4-dichlorobutene-1 from the other isomers can be effected to a high degree by straight distillation, there is, however a small amount of isomerization (principally a thermal isomerization even under reduced pressure conditions) of the remaining cis- and trans-1,4-DCB-2 so that after the cis- and trans-isomers have been separated by distillation a subsequent distillation may be necessary to obtain high purity cis-1,4-DCB-2.

It is a feature of the present invention that an improved vaporization ratio of cis to trans-1,4-dichlorobutene-2 is obtained in distillation to separate the cis and trans-isomers. It is a further feature of the present invention that a distillation process for recovering high purity cis-1,4-dichlorobutene-2, trans-1,4-dichlorobutene-2 and 3,4-dichlorobutene-1 is provided.

DRAWINGS

SUMMARY OF THE INVENTION

Figure 1:
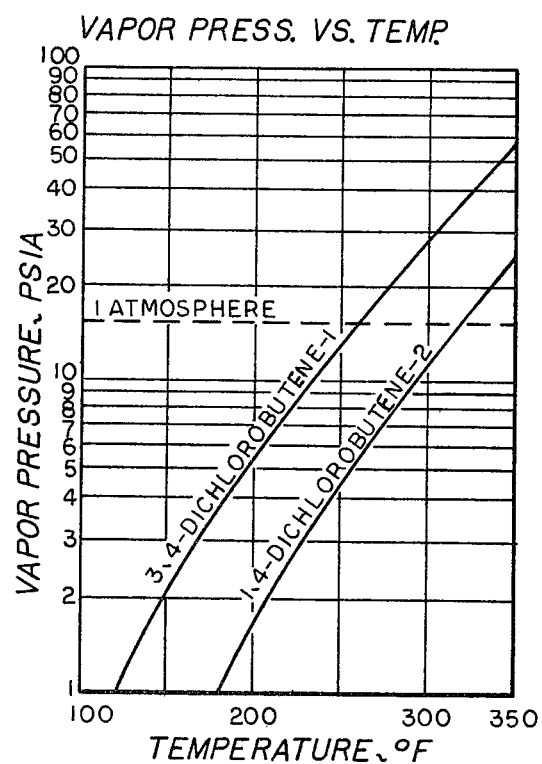
FIG. 1 is a graph showing the relationship of vapor pressure to temperature for 3,4-dichlorobutene-1 and 1,4-dichlorobutene-2.

In one aspect of the present invention it has been discovered that the relative volatility of cis-1,4-dichlorobutene-2 is increased in regard to trans-1,4-dichlorobutene-2 in the presence of 3,4-dichlorobutene-1. In a particular aspect of the present invention it has been found that high purity cis-1,4-dichlorobutene-2 may be recovered from a mixture comprising 10 to 30% cis-1,4-dichlorobutene-2, 30 to 50% trans-1,4-dichlorobutene-2 and 30 to 50%, 3,4-dichlorobutene-1 comprising the steps of fractioning said mixture in a fractionation zone, recovering an overhead fraction containing a major amount, preferably over 50% of the 3,4-dichlorobutene-1, generally 80 to 100% of the 3,4-dichlorobutene-1 in the feed and at least 80% of the cis-1,4-dichlorobutene-2 in the feed and recovering a bottom fraction comprising a major amount, preferably over 70% of the trans-1,4-dichlorobutene-1, generally 90 to 100%, fractioning said overhead fraction in a fractionating zone and recovering a second overhead fraction comprising substantially 3,4-dichlorobutene-1 preferably at least 90% and minor amounts of other materials and recovering a second bottom fraction comprising substantially cis-1,4-dichlorobutene-2, preferably at least 90% and minor amounts of other materials. The bottom fraction from the second column may be further fractionated to bring the cis-isomer up to 99+% purity.

DETAILED DESCRIPTION OF THE INVENTION

The desired product, i.e., the cis-1,4-dichlorobutene-2 which is to be recovered in high purity according to the present invention, is frequently a by-product in the chlorination process of butadiene to produce preferably 3,4-dichlorobutene-1, which is then dehydrochlorinated to produce chloroprene. The racemic mixture of 3,4-dichlorobutene-1, cis-1,4-dichlorobutene-2 and trans-1,4-dichlorobutene-2, will generally comprise from this type of reaction between 30 and 50 wt. % of the 3,4-DCB-1, 10 to 30 wt. % of the cis-1,4-DCB-2 and 30 to 50 wt. % of the trans-1,4-DCB-2. These isomers are generally separated by distillation. For example, the 1,4-dichlorobutene-2 is separated and isomerized to the 3,4-dichlorobutene-1 and used as further feed for the dehydrochlorinations. The relative volatilities of these isomers are 3,4-DCB-1 > cis-1,4-DCB-2 > trans-1,4-DCB-2. Thus, in order to obtain the high purity cis-1,4-DCB-2 an obvious expedient would be to remove the 3,4-DCB-1 since it has a lower boiling point, and to subsequently separate the cis- and the trans-1,4-DCB-2 by distillation. This process, although possibly an obvious approach to a straight forward distillation separation, has a disadvantage in that during the separation of the cis- and trans-isomers, there will be a thermal isomerization in the reboiler portion of the distillation column which results in the production of additional 3,4-DCB-1. Since the 3,4-DCB-1, is a more volatile material than either of the two cis- and trans-1,4-2-isomers, the overhead which is the product richer in the cis-isomer will be again contaminated with the 3,4-DCB-1, which, if a high purity is desired, must be again distilled to separate the cis-1,4-DCB-2 from the isomerized 3,4-DCB-1 in the overheads. Hence, in regard to the present invention the separation of cis-1,4-DCB-2 has an additional advantage beyond the mere improvement of the relative volatility, i.e., increasing the relative volatility of the cis- in regard to the transin the presence of the 3,4-DCB-1, in that the 3,4-DCB-1 need not and as taught by the present invention should not be removed prior to the fractionation of the cis- and trans-isomers. Thus, even if there is isomerization occurring during the fractionation according to the present invention the isomerized 3,4-DCB-1 is for the most part carried overhead along with the 3,4-DCB-1 in the mixture. The overhead portion which is now rich in cis-1,4-DCB-2, particularly as a result of the unique influence of the 3,4-DCB-1 in regard to enhancing the relative volatility of the cis-isomer as compared to the trans-isomer, is fractionated to remove substantially all of the 3,4-DCB-1 as an overhead, which is then handled as described if this operation is related to a neoprene operation, and the bottom portion which is at this point extremely high in the cis-isomer is easily fractionated under less severe conditions to produce cis-isomer and over 90% purity, preferably over 99% purity.

In carrying out the present process, i.e., the fractionation steps therein, normally columns with from 20 to 90 trays would be employed, using reduced pressure in the columns in order to avoid high temperatures, where excessive isomerization of the 1,4-dichlorobutene-2 to 3,4-dichlorobutene-1 occurs. Generally the distillations will be conducted at from less than atmospheric to about 50 mm's of Hg pressure. The boiling point of the 1,4-dichlorobutene-2 cis- form at 760 mm's of Hg is 154° C, and the boiling point of the trans- form at 760 mm's of Hg is 158° C.

FIG. 1 is a table showing the vapor pressure verses temperature for the 3,4-dichlorobutene-1 and 1,4-dichlorobutene-2 and would enable those of skill in the art to appreciate the mechanics of the present invention in regard to the reduced pressure distillations.

The boiling point for 3,4-dichlorobutene-1 at 760 mm's of Hg is 123° C. Hence, it is obvious that whenever a temperature of distillation or fractionation is selected and the distillation conducted in order to maximize the proportion of cis-1,4-dichlorobutene-2 in the overheads, that substantially all of the 3,4-dichlorobutene-1, if present in the fractionation mixture will also be present in the overheads.

Figure 2:
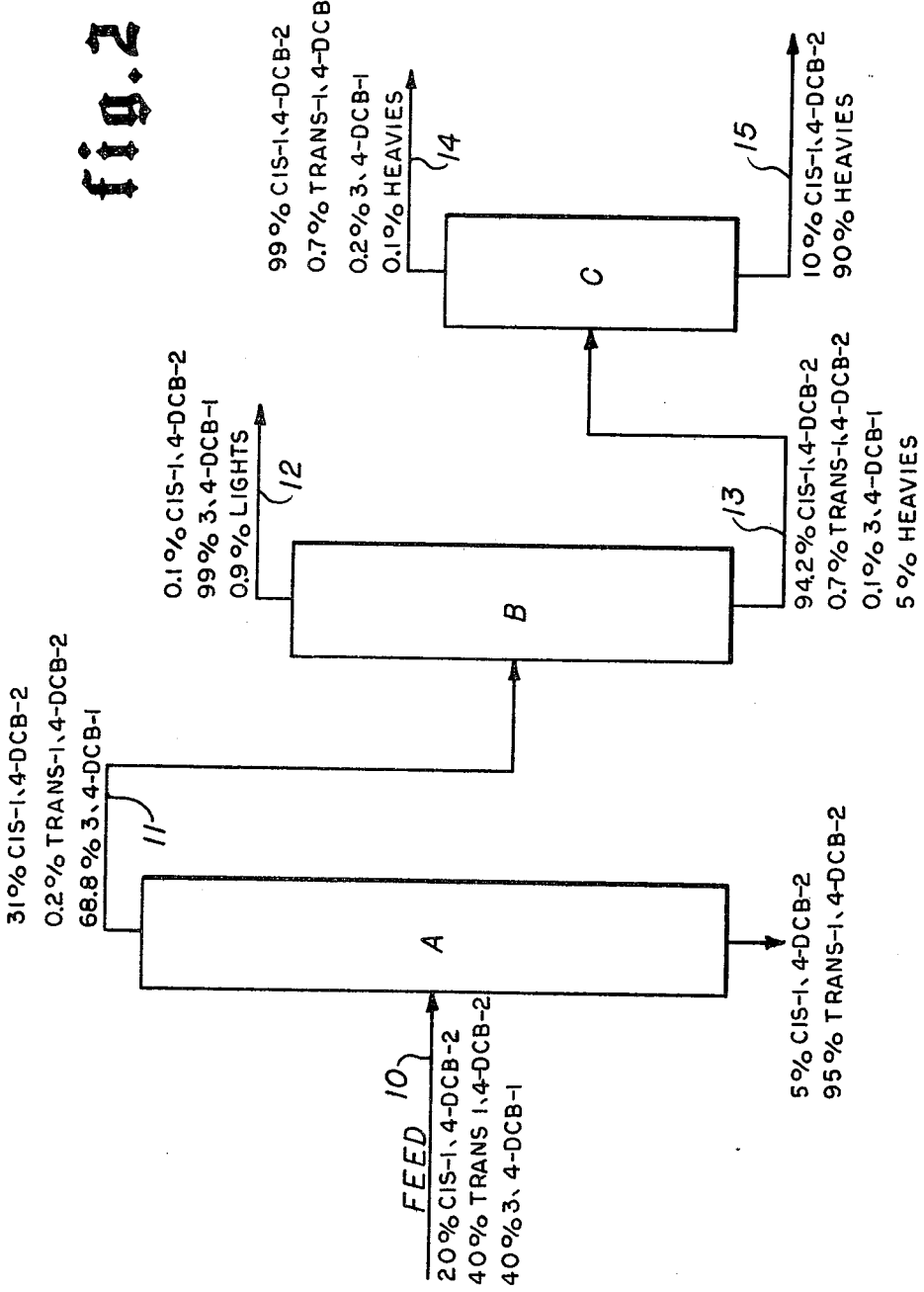
FIG. 2 is a schematic representation of a fractionation employing the present invention.

The present invention may be better understood in its overall application to FIG. 2 which shows a schematic flow diagram for the present distillations. In FIG. 2 a typical constructive distillation is presented. Fractionation, column A is operated at 200 mm's of Hg and has from 70 to 90 trays. The feed which consists of 20% cis-1,4-DCB-2, 40% trans-1,4-DCB-2 and 40% 3,4-DCB-1 is fed to the column through line 10 near the center of the column. Under these conditions the bottoms comprise 5% cis-1,4-DCB-2 and 95% trans-1,4-DCB-2. The bottom fraction may be isomerized to produce a racemic mixture of the cis- and trans- forms and return to the feed stream 10. The overhead, 11, comprise 31% cis-1,4DCB-2 0.2% trans-1,4-DCB-2 and 68.8% 3,4-DCB-1, which is fed to a second distillation column B at approximately the midpoint. This column contains between 30 and 40 trays and is operated at a reflux ratio of 1 : 1, and pressure of 50 mm Hg. The overhead, 12, from column B comprises .1% cis-1,4-DCB-2, 99% 3,4-DCB-1 and 0.9% lights. The lights may be characterized as trichlorinated $C_4$ hydrocarbons. The bottom fraction 13 from column B comprises 94.2% cis-1,4-DCB-2, .7% trans-1,4-DCB-2, 0.1% 3,4-DCB-1 and 5.0% heavies. The heavies may be characterized as tetrachlorinated or higher $C_4$ hydrocarbons. The bottom 13 are fed to column C at approximately the midpoint thereof for further distillation to achieve the high purity cis-isomer. Column C has 10 to 20 trays and is operated at the 1 : 1 reflux ratio, 50 mm's Hg. The bottom 15 comprised 10% cis-1,4-DCB-2 and 90% of the heavies. The overhead 14 comprises 99% cis-1,4-DCB-2, 0.7% trans-1,4-DCB-2, 0.2% 3,4-DCB-1 and 0.1% heavies.

Hence, in this operation the utilization of the present invention in a particular process of recovery of the cis-isomer is demonstrated. What has been avoided is the needless and in fact the detrimental step of first taking out the lowest boiling material, i.e., the 3,4-DCB-1 and subsequent separation of the remaining cis- and trans-1,4-DCB-2 isomers, with a necessary extra separation of the isomerization 3,4-DCB-1 produced during the separation of the cis- and trans-isomers.

The following examples demonstrate the effectiveness, i.e., the synergistic effect of the presence of 3,4-DCB-1 during the fractionation of cis- and trans-1,4-DCB-2. Unless otherwise specified percents herein are weight percents.

EXAMPLES

In the present examples which were carried out in laboratory apparatus, a single column was used for each of the distillations, with the conditions being adjusted as indicated in the Table. The laboratory apparatus was a glass distillation column having a total of 35 trays with the feed inlet being arranged so that 15 trays were below the inlet and 20 trays were above. The column was connected to a vacuum pump so that the pressure therein could be adjusted as indicated in the Table. Example 1 indicates the operation of the column wherein the 3,4-dichlorobutene is not present in the fractionation of the cis-1,4-dichlorobutene-2 and the trans-1,4-dichlorobutene-2. The fraction employed there was obtained by taking the same starting material as used in example 2 (which is according to the present invention) and first fractionating that starting material to remove substantially all of the 3,4-dichlorobutene-1.

TABLE

| Ex. | Feed, Composition, wt % | Reflux Ratio | Pressure mm Hg | Temp. °C Overhead | Temp. °C Bottom | Bottom Composition, wt. % | Overhead Composition, wt. % | % cis/ cis + trans |
|---|---|---|---|---|---|---|---|---|
| 1 | 57.7 Trans-1,4-DCB-2 .06 3,4-DCB-1 42.2 cis-1,4-DCB-2 | 3:1 | 200 | 113 | 120 | 82.35 Trans-1,4-DCB-2 .05 3,4-DCB-1 17.6 cis-1,4-DCB-2 | 31.7 Trans-1,4-DCB-2 2.2 3,4-DCB-1 61.1 cis-1,4-DCB-2 | 67.6 |
| 2 | 40 Trans-1,4-DCB-2 40 3,4-DCB-1 20 cis-1,4-DCB-2 Overhead From Example 2 | 3:1 | 200 | 100 | 119 | 80.9 Trans-1,4-DCB-2 .1 3,4-DCB-1 19 cis-1,4-DCB-2 | 7.7 Trans-1,4-DCB-2 52.5 3,4-DCB-1 39.1 cis-1,4-DCB-2 | 83.5 |
| 3 | 7.7 Trans-1,4-DCB-2 52.5 3,4-DCB-1 39.1 cis-1,4-DCB-2 Overhead From Example 3 | 4:1 | 200 | 90 | 116 | 47.0 cis-1,4-DCB-2 .1 3,4-DCB-1 52.9 trans-1,4-DCB-2 | 20.0 cis-1,4-DCB-2 .37 trans-1,4-DCB-2 78.0 3,4-DCB-1 | |

TABLE-continued

| Ex. | Feed, Composition, wt % | Reflux Ratio | Pressure mm Hg | Temp. °C Overhead | Temp. °C Bottom | Bottom Composition, wt. % | Overhead Composition, wt. % | % cis/ cis + trans |
|---|---|---|---|---|---|---|---|---|
| 4 | 20.0 cis-1,4-DCB-2<br>.37 trans-1,4-DCB-2<br>78.0 3,4-DCB-1 | 1:1 | 100 | 63 | 97 | .7 3,4-DCB-1<br>91.4 cis-1,4-DCB-2<br>1.9 trans-1,4-DCB-2 | 2.6 lights<br>.1 cis-1,4-DCB-2<br>99.3 3,4-DCB-1 | |

It can be seen from the results shown in the Table above that the presence of the 3,4-dichlorobutene-1 in some manner substantially alters the relative volatilities of the cis- and trans- forms in relation to each other, so that there is a greatly improved separation of the cis- and trans-isomers when the 3,4-dichlorobutene-1 is co-distilled with the fraction with the cis-, i.e., the overhead portion of the fractionation. The separation of the cis- and trans-isomers can be appreciated to be very difficult because of the difference of only 4° C in boiling points at atmospheric pressure. Even at reduced pressures, e.g., 20 mm's of Hg the boiling point of cis-1,4-dichlorobutene-2 is only 5° less than that of the trans-1,4-dichlorobutene-2 (55° C and 60° C respectively). In example 1 the presence of 3,4-dichlorobutene-1 in the overhead fraction is the result of isomerization of the 1,4 isomers during the fractionation.

Examples 3 and 4 continue the fractionation of the portion of the distillate materials rich in the cis-isomer through to a fairly high degree of purity, in the laboratory apparatus.

The invention claimed is:

1. The method of recovering cis-1,4-dichlorobutene-2 in high purity comprising fractionating a mixture comprising 10 to 30 wt. % cis-1,4-dichlorobutene-2, 30 to 50 wt. % trans-1,4-dichlorobutene-2, and 30 to 50 wt. % 3,4-dichlorobutene-1 recovering a first overhead fraction containing a major amount of 3,4-dichlorobutene-1 and at least 20 wt. % cis-1,4-dichlorobutene-2 and recovering a first bottom fraction comprising a major amount of trans-1,4-dichlorobutene-2, and
   fractionating said first overhead fraction and recovering a second overhead fraction comprising substantially 3,4-dichlorobutene-1 and a second bottom fraction containing substantially cis-1,4-dichlorobutene-2.

2. The method according to claim 1 wherein said first overhead fraction contains over 50 wt. % of 3,4-dichlorobutene-1 and said first bottom fraction contains over 70 wt. % trans-1,4-dichlorobutene-2.

3. The method according to claim 2 wherein said second overhead fraction contains at least 90 wt. % 3,4-dichlorobutene-1 and said second bottom fraction contains at least 90 wt. % cis-1,4-dichlorobutene-2.

* * * * *